United States Patent
Lee et al.

(10) Patent No.: US 11,820,730 B2
(45) Date of Patent: Nov. 21, 2023

(54) CORE-SHELL COPOLYMER, METHOD FOR PREPARING THE SAME AND THERMOPLASTIC RESIN COMPOSITION CONTAINING THE SAME

(71) Applicant: LG Chem, Ltd., Seoul (KR)

(72) Inventors: Hye Rim Lee, Daejeon (KR); Yoon Ho Kim, Daejeon (KR); Ki Hyun Yoo, Daejeon (KR)

(73) Assignee: LG Chem, Ltd.

( * ) Notice: Subject to any disclaimer, the term of this patent is extended or adjusted under 35 U.S.C. 154(b) by 126 days.

(21) Appl. No.: 16/978,310

(22) PCT Filed: Nov. 13, 2019

(86) PCT No.: PCT/KR2019/015422
§ 371 (c)(1),
(2) Date: Sep. 4, 2020

(87) PCT Pub. No.: WO2020/101342
PCT Pub. Date: May 22, 2020

(65) Prior Publication Data
US 2021/0002193 A1    Jan. 7, 2021

(30) Foreign Application Priority Data

Nov. 16, 2018    (KR) .................. 10-2018-0142092
Nov. 7, 2019    (KR) .................. 10-2019-0141838

(51) Int. Cl.
| | | |
|---|---|---|
| C07C 29/132 | (2006.01) | |
| B01J 19/00 | (2006.01) | |
| B01J 19/18 | (2006.01) | |
| B01J 23/30 | (2006.01) | |
| B01J 23/46 | (2006.01) | |
| C07C 31/20 | (2006.01) | |

(52) U.S. Cl.
CPC ......... *C07C 29/132* (2013.01); *B01J 19/0066* (2013.01); *B01J 19/18* (2013.01); *B01J 23/30* (2013.01); *B01J 23/462* (2013.01); *B01J 2219/00033* (2013.01); *C07C 31/202* (2013.01)

(58) Field of Classification Search
CPC .. C07C 29/132; C07C 31/202; B01J 19/0066; B01J 19/18; B01J 23/30; B01J 23/462; B01J 2219/00033
See application file for complete search history.

(56) References Cited

U.S. PATENT DOCUMENTS

| | | |
|---|---|---|
| 5,132,359 A | 7/1992 | Sasaki et al. |
| 2007/0100073 A1 | 5/2007 | Lee et al. |
| 2008/0097007 A1 | 4/2008 | Lee et al. |
| 2008/0108751 A1 | 5/2008 | Rogunova et al. |
| 2015/0129819 A1 | 5/2015 | Farrand et al. |
| 2016/0194426 A1 | 7/2016 | Yoo et al. |
| 2017/0355843 A1 | 12/2017 | Lee et al. |
| 2017/0362367 A1 | 12/2017 | Petr et al. |

FOREIGN PATENT DOCUMENTS

| | | |
|---|---|---|
| CN | 107001543 A | 8/2017 |
| JP | H11001616 A | 1/1999 |
| JP | H1149961 A | 2/1999 |
| JP | 200086862 A | 3/2000 |
| KR | 100555423 B1 | 2/2006 |
| KR | 100568092 B1 | 4/2006 |
| KR | 20070040939 A | 4/2007 |
| KR | 20090067965 A | 6/2009 |
| KR | 20090086204 A | 8/2009 |
| KR | 20170072089 A | 6/2017 |
| KR | 20170101220 A | 9/2017 |
| KR | 20170141109 A | 12/2017 |
| WO | 2009138388 A1 | 11/2009 |

OTHER PUBLICATIONS

International Search Report for PCT/KR2019/015422 dated Feb. 21, 2020; 2 pages.
Extended European Search Report including Written Opinion for Application No. 19884521.6 dated Apr. 9, 2021, pp. 1-7.

*Primary Examiner* — Alexander R Pagano
(74) *Attorney, Agent, or Firm* — Lerner David LLP

(57) ABSTRACT

A core-shell copolymer, a method of making the same, and a thermoplastic resin including the same are disclosed herein. In some embodiments, a core-shell copolymer including a core and a shell surrounding the core, wherein the core includes a first alkyl(meth)acrylate monomer-derived repeating unit having 1 to 8 carbon atoms and a terminal-modified polydimethylsiloxane crosslinking agent-derived crosslinking part wherein the terminal-modified polydimethylsiloxane crosslinking agent includes a second alkyl(meth)acrylate monomer-derived modified part at both terminals of the polydimethylsiloxane.

15 Claims, No Drawings

CORE-SHELL COPOLYMER, METHOD FOR PREPARING THE SAME AND THERMOPLASTIC RESIN COMPOSITION CONTAINING THE SAME

CROSS-REFERENCE TO RELATED APPLICATIONS

The present application is a national phase entry under 35 U.S.C. § 371 of International Application No. PCT/KR2019/015422, filed on Nov. 13, 2019, which claims priority from Korean Patent Application No. 10-2018-0142092, filed on Nov. 16, 2018 and Korean Patent Application No. 10-2019-0141838, filed on Nov. 7, 2019, the disclosures of which are incorporated herein by reference.

TECHNICAL FIELD

The present invention relates to a core-shell copolymer, and more particularly, to a core-shell copolymer used as an impact modifier of a thermoplastic resin composition, a method for preparing the same, and a thermoplastic resin composition containing the same.

BACKGROUND ART

Automobile exterior materials, cell phone housings, or the like are frequently exposed to cold environments and are easily exposed to light sources such as ultraviolet rays during use. In addition, these materials require a high heat-resistance so as to withstand the hot sun, and a high tensile strength.

In order to develop a thermoplastic resin composition with the above-mentioned properties, products in which a polycarbonate resin having high heat resistance, dimensional stability, and tensile strength is used as a main resin, have been developed.

However, the polycarbonate resin is low in a low-temperature impact strength and a room temperature impact strength, and thus easily broken. In order to compensate for these problems, there have been attempts to increase the impact strength of the polycarbonate resin using an impact modifier.

Examples of the impact modifier used to improve impact strength of the polycarbonate resin include an acrylic-based rubber resin, a butadiene-based rubber resin, a silicone-based rubber resin or the like. The impact modifier is applied depending on properties required by a thermoplastic resin.

However, when an acrylic-based rubber resin is applied as an impact modifier to improve the impact strength of the polycarbonate resin, the polycarbonate resin has an excellent weather resistance and colorability, but has a low glass transition temperature, thereby deteriorating a low-temperature impact strength.

Further, when a butadiene-based rubber resin or a silicone-based rubber resin is applied, the polycarbonate resin has an improved low-temperature impact strength. However, in the case where the butadiene-based rubber resin is used, the polycarbonate resin is easily discolored by external factors such as sunlight, heat, and oxygen due to unsaturated bonds in butadiene rubber, and in the case where the silicone-based rubber resin is used, its coloring is reduced when applied to a polycarbonate resin having a high refractive index due to a low refractive index of the silicone-based resin itself.

Accordingly, research is continuously required to develop the impact modifier with an excellent low-temperature impact strength and room temperature impact strength as well as an excellent colorability when applied to the polycarbonate resin.

DISCLOSURE

Technical Problem

An object of the present invention is to improve impact strength without reducing colorability of the molded article molded from a thermoplastic resin composition containing an impact modifier.

That is, an object of the present invention is to provide a core-shell copolymer having improved impact strength without reducing the colorability of the molded article molded by using a thermoplastic resin composition containing a core-shell copolymer in which a silicone-based polymer whose terminal is modified with a double bond-containing monomer is used as a crosslinking agent of the core, as an impact modifier.

Technical Solution

In one general aspect, there is provided a core-shell copolymer including a core and a shell surrounding the core, wherein the core includes a first alkyl(meth)acrylate monomer-derived repeating unit having 1 to 8 carbon atoms and a terminal-modified polydimethylsiloxane crosslinking agent-derived crosslinking part; and the terminal-modified polydimethylsiloxane crosslinking agent includes a second alkyl(meth)acrylate monomer-derived modified part at both terminals of the polydimethylsiloxane.

In other general aspect, there is provided a method for preparing a core-shell copolymer, including: preparing a core by polymerizing a core-forming mixture including a first alkyl(meth)acrylate monomer having 1 to 8 carbon atoms and a terminal-modified polydimethylsiloxane; and preparing a core-shell copolymer by polymerizing a shell-forming mixture in the presence of the prepared core, wherein the terminal-modified polydimethylsiloxane includes a second alkyl(meth)acrylate monomer-derived modified part at both terminals of the polydimethylsiloxane.

In another general aspect, there is provided a thermoplastic resin composition containing the core-shell copolymer and a polycarbonate resin.

Advantageous Effects

In the present invention, when the core-shell copolymer is used as an impact modifier, the molded article molded from the thermoplastic resin composition containing the core-shell copolymer has an excellent impact strength, particularly, an excellent low-temperature impact strength, without reducing colorability.

BEST MODE

The terms and words used in the detailed description and claims should not be interpreted as being limited to conventional or dictionary meanings, but should be interpreted as having meanings and concepts meeting the technical ideas of the present invention based on a principle that the inventors can appropriately define the concepts of terms in order to describe their own inventions in the best mode.

The term "monomer-derived repeating unit" used herein may refer to a monomer-derived component, a structure thereof, or a substance itself. Specific examples thereof may refer to a repeating unit in which the monomer to be added participates in the polymerization reaction and is formed in the polymer, during polymerization of the polymer.

The term "crosslinking agent-derived crosslinking part" used herein may refer to a component derived from compounds used as the crosslinking agent, a structure thereof, or a substance itself, and may refer to a crosslinking part which performs a role of crosslinking in or between polymers formed by the action and reaction of a crosslinking agent.

The term "seed" used herein may refer to a polymer component or copolymer component first polymerized prior to polymerization of the core during the preparing process so as to complement mechanical physical properties of the core-shell copolymer, facilitate the polymerization of the core, and adjust an average particle diameter of the core.

The term "core" used herein may refer to a polymer component or copolymer component in which the monomer forming the core is polymerized to form a core or core layer of the core-shell copolymer. Also, the term "core" may refer to a polymer component or a copolymer component in which the monomer forming the core is formed on the seed to form a core or a core layer that exhibits a form in which the core surrounds the seed.

The term "shell" used herein may refer to a polymer component or copolymer component in which the monomer forming the shell is graft polymerized on the core of the core-shell copolymer to form a shell or shell layer of the core-shell copolymer that exhibits a form in which the shell surrounds the core.

Hereinafter, the present invention will be described in more detail to assist in understanding the technical idea of the present invention.

<Core-Shell Copolymer>

The core-shell copolymer according to the present invention may include a core and a shell surrounding the core.

The core may include a first alkyl(meth)acrylate monomer-derived repeating unit having 1 to 8 carbon atoms and a terminal-modified polydimethylsiloxane crosslinking agent-derived crosslinking part.

The first alkyl(meth)acrylate monomer is a component which improves a room temperature impact strength of the polycarbonate resin, and may be an alkyl(meth)acrylate monomer containing an alkyl group having 1 to 8 carbon atoms. In this case, the alkyl group having 1 to 8 carbon atoms may refer to both a linear alkyl group having 1 to 8 carbon atoms and a branched alkyl group having 3 to 8 carbon atoms. Specific examples of the alkyl(meth)acrylate monomer may include methyl(meth)acrylate, ethyl(meth)acrylate, propyl(meth)acrylate, buty (meth)acrylate, pentyl(meth)acrylate, hexyl(meth)acrylate, heptyl(meth)acrylate, (meth)acrylate, octyl(meth)acrylate, or 2-ethylhexyl(meth)acrylate. Here, the first alkyl(meth)acrylate monomer may refer to alkyl acrylate or alkyl methacrylate.

The content of the first alkyl(meth)acrylate monomer-derived repeating unit may be 70 parts by weight to 95 parts by weight, 80 parts by weight to 92 parts by weight, or 83 parts by weight to 88 parts by weight, based on a total of 100 parts by weight of the core-shell copolymer. Within the above-mentioned range, the molded article molded by using the thermoplastic resin composition containing the core-shell copolymer according to the present invention as an impact modifier, has an excellent colorability and impact strength.

The terminal-modified polydimethylsiloxane crosslinking agent is a component for crosslinking the first alkyl(meth) acrylate monomer-derived repeating unit, and may include a second alkyl(meth)acrylate monomer-derived modified part at both terminals of the polydimethylsiloxane.

Specifically, the terminal-modified polydimethylsiloxane crosslinking agent may include a compound represented by the following Formula 1:

[Formula 1]

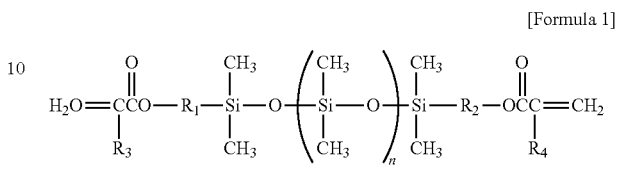

where $R_1$ and $R_2$ are each independently an alkylene group having 1 to 30 carbon atoms, an alkylene group having 1 to 20 carbon atoms, or an alkylene group having 1 to 8 carbon atoms, $R_3$ and $R_4$ are each independently hydrogen or a methyl group, and n is 5 to 400, 5 to 360, or 10 to 330.

Meanwhile, in the case of a core-shell copolymer prepared by using an acrylic-based resin (e.g., ethylene glycol dimethacrylate) containing a double bond at both terminals as a crosslinking agent, impact strength at low-temperatures is poor because the acrylic-based resin itself has a glass transition temperature of about −40° C. to −50° C. However, since the core-shell copolymer of the present invention has a terminal-modified polydimethylsiloxane including an alkyl(meth)acrylate-derived modified part at both terminals of the polydimethylsiloxane as a crosslinking agent and the polydimethylsiloxane itself has a glass transition temperature of −100° C. to −120° C., the molded article molded by using the thermoplastic resin composition containing the core-shell copolymer according to the present invention as an impact modifier has an excellent colorability and impact strength.

The content of the terminal-modified polydimethylsiloxane crosslinking agent-derived crosslinking part may be 0.01 parts by weight to 5 parts by weight, 0.01 parts by weight to 2 parts by weight, or 0.1 parts by weight to 2 parts by weight, based on a total of 100 parts by weight of the core-shell copolymer. Within the above-mentioned range, the molded article molded by using the thermoplastic resin composition containing the core-shell copolymer according to the present invention as an impact modifier, has an excellent colorability and impact strength.

The core may be a component for easily grafting the shell on the core, and may further include a first crosslinkable monomer-derived repeating unit together with a first alkyl(meth)acrylate monomer-derived repeating unit having 1 to 8 carbon atoms and a terminal-modified polydimethylsiloxane crosslinking agent-derived crosslinking part.

Specific examples of the first crosslinkable monomer may include at least one selected from (meth)acrylic-based crosslinkable monomers such as ethylene glycol di(meth)acrylate, 1,6-hexanediol di(meth)acrylate, allyl(meth)acrylate, trimethylolpropane tri(meth)acrylate, and pentaerythritol tetra(meth)acrylate; and vinyl-based crosslinkable monomers such as divinylbenzene, divinyl naphthalene, and diallyl phthalate.

When the core includes a first crosslinkable monomer-derived repeating unit, the content of the first crosslinkable monomer-derived repeating unit may be 0.01 parts by weight to 5 parts by weight, 0.01 parts by weight to 2 parts by weight, or 0.1 parts by weight to 2 parts by weight, based on a total of 100 parts by weight of the core-shell copolymer.

Within the above-mentioned range, the shell may be easily grafted on the core, and the molded article molded by using the thermoplastic resin composition containing the core-shell copolymer according to the present invention as an impact modifier, has an excellent colorability and impact strength.

Meanwhile, the core may include a seed including a fourth alkyl(meth)acrylate monomer-derived repeating unit having 1 to 8 carbon atoms to adjust an average particle diameter of the core. As a specific example, the core may include a core surrounding the seed.

The seed may further include a second crosslinkable monomer-derived repeating unit together with a fourth alkyl (meth)acrylate monomer-derived repeating unit having 1 to 8 carbon atoms to easily form a core on the seed. The fourth alkyl(meth)acrylate monomer-derived repeating unit and the second crosslinkable monomer-derived repeating unit included in the seed may be the same as the type of each monomer, specifically, the first alkyl(meth)acrylate and the first crosslinkable monomer, for forming the monomer-derived repeating unit included in the core described above.

When the core includes the seed, the content of the seed may be 0.5 parts by weight to 20 parts by weight, 5 parts by weight to 18 parts by weight, or 5.8 parts by weight to 15.5 parts by weight, based on a total of 100 parts by weight of the core-shell copolymer. Within the above-mentioned range, an average particle diameter of the core may be easily adjusted.

In addition, when the core includes the seed, the content of a first alkyl(meth)acrylate monomer-derived repeating unit included in the core may include the content of a fourth alkyl(meth)acrylate monomer-derived repeating unit included in the seed, and the content of a first crosslinkable monomer-derived repeating unit included in the core may include the content of a second crosslinkable monomer-derived repeating unit included in the seed.

As a specific example, the content of the fourth alkyl (meth)acrylate monomer-derived repeating unit may be 90 parts by weight to 99.5 parts by weight, 92 parts by weight to 98 parts by weight, or 93 parts by weight to 96 parts by weight, based on a total of 100 parts by weight of the seed. Within the above-mentioned range, impact strength is excellent and compatibility with the core is excellent.

In addition, the content of the second crosslinkable monomer-derived repeating unit may be 0.5 parts by weight to 10 parts by weight, 2 parts by weight to 8 parts by weight, or 4 parts by weight to 7 parts by weight, based on a total weight of the seed. Within the above-mentioned range, a large-diameter particle of the core may be easily prepared.

The core according to the present invention may have an average particle diameter of 150 nm to 500 nm, 150 nm to 300 nm, or 185 nm to 260 nm. Within the above-mentioned range, the molded article molded by using a thermoplastic resin composition containing the core-shell copolymer according to the present invention as an impact modifier, has an excellent gloss, colorability, and impact strength.

The shell may be formed by graft polymerization of at least one monomer-derived repeating unit selected from the group consisting of a third alkyl(meth)acrylate monomer-derived repeating unit and an aromatic vinyl monomer-derived repeating unit on the core. As a specific example, the shell of the present invention may include a third alkyl (meth)acrylate monomer-derived repeating unit or an aromatic vinyl monomer-derived repeating unit, or a third alkyl(meth)acrylate monomer-derived repeating unit and an aromatic vinyl monomer-derived repeating unit.

The third alkyl(meth)acrylate monomer is a component which imparts compatibility between a polycarbonate resin and the core, and may be an alkyl(meth)acrylate monomer containing an alkyl group having 1 to 8 carbon atoms. In this case, the alkyl group having 1 to 8 carbon atoms may refer to both a linear alkyl group having 1 to 8 carbon atoms and a branched alkyl group having 3 to 8 carbon atoms. Specific examples of the alkyl(meth)acrylate monomer may include methyl(meth)acrylate, ethyl(meth)acrylate, propyl(meth) acrylate, butyl(meth)acrylate, pentyl(meth)acrylate, hexyl (meth)acrylate, heptyl(meth)acrylate, octyl(meth)acrylate, or 2-ethylhexyl(meth)acrylate. Here, the third alkyl(meth) acrylate monomer may refer to alkyl acrylate or alkyl methacrylate, and the third alkyl(meth)acrylate monomer may be identical or different from the first alkyl(meth) acrylate monomer or the second alkyl(meth)acrylate monomer.

The aromatic vinyl monomer imparts compatibility between a thermoplastic resin and the core, and has a high refractive index. Thus, when the core-shell copolymer containing the aromatic vinyl monomer is used as an impact modifier, as a component for improving colorability of the thermoplastic resin, styrene, alphamethylstyrene, 3-methyl styrene, 4-methyl styrene, 4-propyl styrene, isopropenyl naphthalene, 1-vinylnaphthalene, styrene substituted with an alkyl group having 1 to 3 carbon atoms, 4-cyclohexyl styrene, 4-(p-methylphenyl) styrene, halogen-substituted styrenes, or a combination thereof may be used.

The content of at least one monomer-derived repeating unit selected from the group consisting of the third alkyl (meth)acrylate monomer-derived repeating unit and the aromatic vinyl monomer-derived repeating unit may be 5 parts by weight to 30 parts by weight, 10 parts by weight to 25 parts by weight, or 10 parts by weight to 20 parts by weight, based on a total of 100 parts by weight of the core-shell copolymer. Within the above-mentioned range, the molded article molded by using the thermoplastic resin composition containing the core-shell copolymer according to the present invention as an impact modifier, has an excellent colorability and impact strength.

That is, the core-shell copolymer of the present invention may include 70 parts by weight to 95 parts by weight, 80 parts by weight to 90 parts by weight, or 85 parts by weight to 90 parts by weight of the core, and 5 parts by weight to 30 parts by weight, 10 parts by weight to 25 parts by weight, or 10 parts by weight to 20 parts by weight of the shell, based on a total of 100 parts by weight of the core-shell copolymer. Within the above-mentioned range, the molded article molded by using the thermoplastic resin composition containing the core-shell copolymer according to the present invention as an impact modifier, has an excellent colorability and impact strength.

<Method for Preparing Core-Shell Copolymer>

A method for preparing a core-shell copolymer according to the present invention may include preparing a core by polymerizing a core-forming mixture including a first alkyl (meth)acrylate monomer having 1 to 8 carbon atoms and a terminal-modified polydimethylsiloxane; and preparing a core-shell copolymer by polymerizing a shell-forming mixture in the presence of the prepared core, wherein the terminal-modified polydimethylsiloxane includes a second alkyl(meth)acrylate monomer-derived modified part at both terminals of the polydimethylsiloxane. The prepared core may have an average particle diameter of 150 nm to 500 nm.

The method for preparing the core-shell copolymer may include stepwisely preparing the core and the shell by the preparing of the core and the preparing of the core-shell copolymer, respectively, and then polymerizing the core and the shell. The core of the core-shell copolymer may be polymerized by the preparing of the core, and the shell may be then polymerized on the core by the preparing of the core-shell copolymer.

The preparing of the core may be preparing the core of the core-shell copolymer, and the type and content of each monomer in the core-forming mixture added in the preparing of the core may be the same as the type and content of each monomer for forming the monomer-derived repeating unit included in the core described above.

Meanwhile, the preparing of the core may include preparing a seed; and preparing a core by polymerizing a core-forming mixture including a first alkyl(meth)acrylate monomer having 1 to 8 carbon atoms and a terminal-modified polydimethylsiloxane in the presence of the prepared seed.

The preparing of the seed is for facilitating polymerization of the core and adjusting an average particle diameter of the core when the core-shell copolymer is polymerized, and may be performed by radical polymerization in the presence of a fourth alkyl(meth)acrylate monomer having 1 to 8 carbon atoms and a second crosslinkable monomer, and may be performed by an emulsion polymerization method. In addition, the polymerization may be performed by further using additives such as initiators, emulsifiers, molecular weight regulators, activators, redox catalysts, and ion exchange water.

In addition, the preparing of the seed may be performed at a temperature of 45° C. to 65° C., 48° C. to 62° C., or 50° C. to 60° C.

The fourth alkyl(meth)acrylate monomer and the second crosslinkable monomer included in the seed may be the same as the type of each monomer, specifically, the first alkyl(meth)acrylate and the first crosslinkable monomer, for forming the monomer-derived repeating unit included in the core described above.

In addition, the preparing of the core-shell copolymer may be preparing of the shell of the core-shell copolymer, and the type and content of each monomer in the shell-forming mixture added in the preparing of the core-shell copolymer may be the same as the type and content of each monomer for forming each monomer-derived repeating unit included on the shell described above.

The polymerization in the preparing of the seed, the preparing of the core, and the preparing of the core-shell copolymer may be performed by using methods such as emulsion polymerization, bulk polymerization, suspension polymerization, and solution polymerization, and may be polymerized further using additives such as initiators, emulsifiers, molecular weight regulators, activators, redox catalysts, and ion exchanged water.

The initiators may be, for example, but are not limited to, inorganic peroxides such as sodium persulfate, potassium persulfate, ammonium persulfate, potassium perphosphate, and hydrogen peroxide; organic peroxides such as t-butyl hydroperoxide, cumene hydroperoxide, p-menthane hydroperoxide, di-t-butyl peroxide, t-butylcumyl peroxide, acetyl peroxide, isobutyl peroxide, octanoyl peroxide, dibenzoyl peroxide, 3,5,5-trimethylhexanol peroxide, and t-butyl peroxy isobutylate; and nitrogen compounds such as azobis isobutyronitrile, azobis-2,4-dimethylvaleronitrile, azobiscyclohexanecarbonitrile, and azobis methyl isobutyrate. Such initiators may be used in an amount of 0.03 parts by weight to 0.2 parts by weight, based on a total of 100 parts by weight of the seed or a total of 100 parts by weight of the core-shell copolymer.

The emulsifiers may be at least one selected from the group consisting of anionic emulsifiers, cationic emulsifiers, and nonionic emulsifiers. For example, the emulsifiers may be at least one selected from the group consisting of, but are not limited to, anionic emulsifiers widely used in emulsifying polymerization, such as sulfonates, carboxylates, succinates, sulfosuccinates, and metal salts thereof, for example, alkylbenzenesulfonic acid, sodium alkylbenzene sulfonate, akylsulfonic acid, sodium alkylsulfonate, sodium polyoxyethylene nonylphenylether sulfonate, sodium stearate, sodium dodecyl sulfate, sodium dodecyl benzene sulfonate, sodium lauryl sulfate, sodium dodecyl sulfosuccinate, potassium oleate, and abietinate; cationic emulsifiers in which amine halides, alkyl tetraammonium salts, alkylpyridinium salts, or the like are bonded as functional groups of higher aliphatic hydrocarbons; and nonionic emulsifiers such as polyvinyl alcohol and polyoxyethylene nonylphenyl. Such emulsifiers may be used in an amount of 0.1 parts by weight to 5 parts by weight, based on a total of 100 parts by weight of the seed or a total of 100 parts by weight of the core-shell copolymer.

The molecular weight regulators, for example, may be, but are not limited to, mercaptans such as a-methylstyrene dimer, t-dodecyl mercaptan, n-dodecyl mercaptan, and octyl mercaptan; halogenated hydrocarbons such as carbon tetrachloride, methylene chloride, and methylene bromide; and sulfur-containing compounds such as tetraethyl thiuram disulfide, dipentamethylene thiuram disulfide, and diisopropylxanthogen disulfide. Such molecular weight regulators may be used in an amount of 0.1 parts by weight to 3 parts by weight, based on a total of 100 parts by weight of the seed or a total of 100 parts by weight of the core-shell copolymer.

The activators, for example, may be at least one selected from the group consisting of, but are not limited to, sodium hydrosulfite, sodium formaldehyde sulfoxylate, sodium ethylenediamine tetraacetate, ferrous sulfate, lactose, dextrose, sodium linoleate, and sodium sulfate. Such activators may be used in an amount of 0.01 parts by weight to 0.15 parts by weight, based on a total of 100 parts by weight of the seed or a total of 100 parts by weight of the core-shell copolymer.

The redox catalysts, for example, may be, but are not limited to, sodium formaldehyde sulfoxylate, ferrous sulfate, disodium ethylenediamine tetraacetate, cupric sulfate, or the like. Such redox catalysts may be used in an amount of 0.01 parts by weight to 0.1 parts by weight, based on a total of 100 parts by weight of the seed or a total of 100 parts by weight of the core-shell copolymer.

In addition, the core and the core-shell copolymer prepared in the preparing of the core and the preparing of the core-shell copolymer may be obtained in the form of core latex and core-shell copolymer latex in which the core and core-shell copolymer are dispersed in a solvent, respectively. In order to obtain the core-shell copolymer from the core-shell copolymer in the form of powder, processes such as agglomeration, aging, dehydration and drying may be performed.

<Thermoplastic Resin Composition>

The thermoplastic resin composition according to the present invention may contain the core-shell copolymer as an impact modifier, and may contain a polycarbonate resin. That is, the thermoplastic resin composition may be a polycarbonate resin composition.

The thermoplastic resin composition may contain 1 part by weight to 20 parts by weight, 1 part by weight to 15 parts by weight, or 1 part by weight to 10 parts by weight of the core-shell copolymer, based on 100 parts by weight of the polycarbonate resin. Within the above-mentioned range, the molded article molded from the thermoplastic resin composition has an excellent colorability and impact strength.

The thermoplastic resin composition according to the present invention may further contain, in addition to the core-shell copolymer and the polycarbonate resin, additives such as flame retardants, lubricants, antioxidants, light stabilizers, reaction catalysts, mold release agents, pigments, antistatic agents, conductivity imparting agents, EMI shields, magnetizing agents, crosslinking agents, antibacterial agents, processing aids, metal deactivators, smoke suppressants, fluorine-based anti-drip agents, inorganic fillers, glass fibers, anti-friction agents, anti-wear agents, and coupling agents, within the range in which physical properties are not deteriorated, if necessary.

The methods of melt kneading and processing the thermoplastic resin composition are not particularly limited. However, as an example, the thermoplastic resin composition was first mixed in a supermixer, and then melt kneaded by using one of ordinary blending equipments such as a twin screw extruder, a single screw extruder, a roll mill, a kneader, or a Banbury mixer to obtain pellets by using a pelletizer. Thereafter, the resulting pellets may be sufficiently dried with a dehumidifying dryer or a hot air dryer, followed by injection processing to obtain a final molded article.

Hereinafter, the present invention will be described in detail with reference to the following examples. However, the following examples describe the present invention by way of example only. It is apparent to those skilled in the art that various changes and modifications can be made in the scope and spirit of the present invention and that the present invention is not limited thereto.

EXAMPLES

Example 1

<Preparation of Seed>

Into a nitrogen-substituted polymerization reactor, 50 parts by weight of distilled water, 0.9 parts by weight of sodium lauryl sulfate (SLS), 11 parts by weight of n-butyl acrylate (BA), and 0.05 parts by weight of allyl methacrylate (AMA) were added in a batch, and an internal temperature of the reactor was raised to 50° C. When the internal temperature of the reactor reached 50° C., 0.005 parts by weight of ferrous sulfate (FeS), 0.03 parts by weight of disodium ethylenediamine tetraacetate (EDTA). 0.25 parts by weight of sodium formaldehyde sulfoxylate (SFS), and 0.04 parts by weight of t-butyl hydroperoxide (TBHP) were added in a batch thereto and reacted for 1 hour.

Into a separate reactor, 50 parts by weight of distilled water, 0.45 parts by weight of sodium lauryl sulfate, 88.5 parts by weight of butyl acrylate, and 0.45 parts by weight of allyl methacrylate were added to prepare a pre-emulsion as a monomer. Into the nitrogen-substituted polymerization reactor, 0.01 parts by weight of ferrous sulfate (FeS), 0.05 parts by weight of disodium ethylenediamine tetraacetate, 0.5 parts by weight of sodium formaldehyde sulfoxylate, and 0.1 parts by weight of t-butyl hydroperoxide together with the prepared pre-emulsion were added for 5 hours under the internal temperature of 50° C. to polymerize them, thereby obtaining a latex including a seed. After the reaction was completed, the seed particle distributed on the latex had an average particle diameter of 100 nm.

<Preparation of Core>

Into a nitrogen-substituted polymerization reactor, 30 parts by weight of distilled water and 15.5 parts by weight (based on solids) of the prepared seed were added, and an internal temperature of the reactor was raised to 55° C. When the internal temperature of the reactor reached 55° C., a core-forming mixture obtained by mixing 73 parts by weight of butyl acrylate, 1.0 part by weight of a terminal-modified polydimethylsiloxane crosslinking agent (n=10) represented by the following Formula 2, 0.5 parts by weight of aryl methacrylate, 30 parts by weight of distilled water, 0.3 parts by weight of sodium lauryl sulfate, 0.01 parts by weight of ferrous sulfate, 0.05 parts by weight of sodium ethylene diamine tetraacetate, 0.5 parts by weight of sodium formaldehyde sulfoxylate, and 0.1 parts by weight of t-butyl hydroperoxide based on a total of 100 parts by weight of the core-shell copolymer, was added thereto for 5 hours to obtain a latex including a core. The core in the latex had an average particle diameter of 186 nm.

[Formula 2]
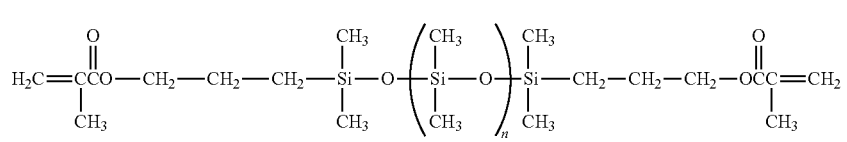

<Preparation of Core-Shell Copolymer>

Into a nitrogen-substituted polymerization reactor, a shell-forming mixture obtained by mixing 10 parts by weight of methyl methacrylate, 10 parts by weight of distilled water, 0.01 parts by weight of sodium lauryl sulfate, 0.01 parts by weight of ferrous sulfate, 0.05 parts by weight of sodium ethylene diamine tetraacetate, 0.5 parts by weight of sodium formaldehyde sulfoxylate, and 0.1 parts by weight of t-butyl hydroperoxide, was added to 90 parts by weight (based on solids) of the latex including the obtained core, and graft polymerization was performed at 60° C. for 2 hours to obtain a latex including a core-shell copolymer.

<Preparation of Core-Shell Copolymer Powder>

The latex including the obtained core-shell copolymer was diluted in distilled water to have 15 wt % based on solids, placed in a coagulation bath, and then an internal temperature of the coagulation bath was raised to 70° C. Then, 4 parts by weight of a calcium chloride solution was added to the latex including the core-shell copolymer, based on 100 parts by weight of solids, and the resulting mixture was agglomerated with stirring. Thereafter, the copolymer and water were separated, and then dehydrated and dried to obtain a core-shell copolymer powder.

Example 2

Example 2 was performed identically to Example 1, except that in the preparation of the core, 1.0 part by weight of a terminal-modified polydimethylsiloxane crosslinking agent (n=69) represented by Formula 2 was added instead of 1.0 part by weight of a terminal-modified polydimethylsiloxane crosslinking agent (n=10) represented by Formula 2 in the core-forming monomer mixture.

Example 3

Example 3 was performed identically to Example 1, except that in the preparation of the core, 5.8 parts by weight of the seed was added instead of 15.5 parts by weight, 82.2 parts by weight of butyl acrylate was added instead of 73 parts by weight, and 1.5 parts by weight of a terminal-modified polydimethylsiloxane crosslinking agent (n=69) represented by Formula 2 was added instead of 1.0 part by weight of a terminal-modified polydimethylsiloxane crosslinking agent (n=10) represented by Formula 2 in the core-forming monomer mixture.

Example 4

Example 4 was performed identically to Example 1, except that in the preparation of the core, 5.8 parts by weight of the seed was added instead of 15.5 parts by weight, 82.2 parts by weight of butyl acrylate was added instead of 73 parts by weight, and 1.5 parts by weight of a terminal-modified polydimethylsiloxane crosslinking agent (n=120) represented by Formula 2 was added instead of 1.0 part by weight of a terminal-modified polydimethylsiloxane crosslinking agent (n=10) represented by Formula 2 in the core-forming monomer mixture.

Example 5

Example 5 was performed identically to Example 1, except that in the preparation of the core, 5.8 parts by weight of the seed was added instead of 15.5 parts by weight, 82.2 parts by weight of butyl acrylate was added instead of 73 parts by weight, and 1.5 parts by weight of a terminal-modified polydimethylsiloxane crosslinking agent (n=330) represented by Formula 2 was added instead of 1.0 part by weight of a terminal-modified polydimethylsiloxane crosslinking agent (n=10) represented by Formula 2 in the core-forming monomer mixture.

Example 6

Example 6 was performed identically to Example 1, except that in the preparation of the core, 5.8 parts by weight of the seed was added instead of 15.5 parts by weight, 82.2 parts by weight of butyl acrylate was added instead of 73 parts by weight, and 1.5 parts by weight of a terminal-modified polydimethylsiloxane crosslinking agent (n=2) represented by Formula 2 was added instead of 1.0 part by weight of a terminal-modified polydimethylsiloxane crosslinking agent (n=10) represented by Formula 2 in the core-forming monomer mixture.

Example 7

Example 7 was performed identically to Example 1, except that in the preparation of the core, 5.8 parts by weight of the seed was added instead of 15.5 parts by weight, 82.2 parts by weight of butyl acrylate was added instead of 73 parts by weight, and 1.5 parts by weight of a terminal-modified polydimethylsiloxane crosslinking agent (n=400) represented by Formula 2 was added instead of 1.0 part by weight of a terminal-modified polydimethylsiloxane crosslinking agent (n=10) represented by Formula 2 in the core-forming monomer mixture.

Comparative Example 1

Comparative Example 1 was performed identically to Example 1, except that in the preparation of the core, 1.0 part by weight of ethylene glycol dimethacrylate was added instead of 1.0 part by weight of a terminal-modified polydimethylsiloxane crosslinking agent (n=10) represented by Formula 2 in the core-forming monomer mixture.

Comparative Example 2

Comparative Example 2 was performed identically to Example 1, except that in the preparation of the core, 5.8 parts by weight of the seed was added instead of 15.5 parts by weight, 82.2 parts by weight of butyl acrylate was added instead of 73 parts by weight, and 1.5 parts by weight of ethylene glycol dimethacrylate was added instead of 1.0 part by weight of a terminal-modified polydimethylsiloxane crosslinking agent (n=10) represented by Formula 2 in the core-forming monomer mixture.

Comparative Example 3

Comparative Example 3 was performed identically to Example 1, except that in the preparation of the core, 5.8 parts by weight of the seed was added instead of 15.5 parts by weight, 82.2 parts by weight of butyl acrylate was added instead of 73 parts by weight, and 1.5 parts by weight of ethylene glycol dimethacrylate was added instead of 1.0 part by weight of a terminal-modified polydimethylsiloxane crosslinking agent (n=10) represented by Formula 2 in the core-forming monomer mixture, and in the preparation of the core-shell copolymer, 9 parts by weight of methyl methacrylate was added instead of 10 parts by weight, and 1 part by weight of a terminal-modified polydimethylsiloxane crosslinking agent represented by Formula 2 was further added in the shell-forming monomer mixture.

Comparative Example 4

Comparative Example 4 was performed identically to Example 1, except that in the preparation of the core, 0.4 parts by weight of the seed was added instead of 15.5 parts by weight, 87.6 parts by weight of butyl acrylate was added instead of 73 parts by weight, and 1.5 parts by weight of a terminal-modified polydimethylsiloxane crosslinking agent (n=69) represented by Formula 2 was added instead of 1.0 part by weight of a terminal-modified polydimethylsiloxane crosslinking agent (n=10) represented by Formula 2 in the core-forming monomer mixture.

EXPERIMENTAL EXAMPLE

Experimental Example 1

The average particle diameters of the core and the core-shell copolymer prepared in Examples 1 to 7 and Comparative Examples 1 to 4 were measured by the following methods, and the composition of the core-shell copolymer composition together with the results is shown in Tables 1 and 2 below.

Average particle diameter (D50, nm): A sample obtained by diluting the latex including the prepared core to 200 ppm or less was prepared. Thereafter, the average particle diameter (D50) of the core particles dispersed in the latex including the core was measured according to the intensity Gaussian distribution by dynamic laser light scattering method using Nicomp 380 at room temperature (23° C.)

maintained at room temperature (23° C.) and low-temperature (−30° C.) After aging the ⅛ inch notched specimen in each chamber for 6 hours, the specimen was removed and evaluated by the ASTM D256 test method.

TABLE 1

| | | Examples | | | | | | |
|---|---|---|---|---|---|---|---|---|
| | Classification | 1 | 2 | 3 | 4 | 5 | 6 | 7 |
| Core | Seed contents (parts by weight) | 15.5 | 15.5 | 5.8 | 5.8 | 5.8 | 5.8 | 5.8 |
| | BA contents (parts by weight) | 73 | 73 | 82.2 | 82.2 | 82.2 | 82.2 | 82.2 |
| | MTPDS    n | 10 | 69 | 69 | 120 | 330 | 2 | 400 |
| | (parts by weight)  Contents | 1.0 | 1.0 | 1.5 | 1.5 | 1.5 | 1.5 | 1.5 |
| | EGDMA (parts by weight) | — | — | — | — | — | — | — |
| | AMA (parts by weight) | 0.5 | 0.5 | 0.5 | 0.5 | 0.5 | 0.5 | 0.5 |
| Shell | MMA contents (parts by weight) | 10 | 10 | 10 | 10 | 10 | 10 | 10 |
| | Average particle diameter of core (nm) | 186 | 185 | 258 | 260 | 260 | 260 | 258 |

BA: butyl acrylate
MTPDS: terminal-modified polydimethylsiloxane crosslinking agent
EGDMA: ethylene glycol dimethacrylate
AMA: allyl methacrylate
MMA: methyl methacrylate

TABLE 2

| | | Comparative Examples | | | |
|---|---|---|---|---|---|
| | Classification | 1 | 2 | 3 | 4 |
| Core | Seed contents (parts by weight) | 15.5 | 5.8 | 5.8 | 0.4 |
| | BA contents (parts by weight) | 73 | 82.2 | 82.2 | 87.6 |
| | MTPDS    n | — | — | — | 69 |
| | (parts by weight)  Contents | — | — | — | 1.5 |
| | EGDMA (parts by weight) | 1.0 | 1.5 | 1.5 | — |
| | AMA (parts by weight) | 0.5 | 0.5 | 0.5 | 0.5 |
| Shell | MMA contents (parts by weight) | 10 | 10 | 9 | 10 |
| | MTPDS    n | — | — | 69 | — |
| | (parts by weight)  Contents | — | — | 1 | — |
| | Average particle diameter of core (nm) | 185 | 260 | 262 | 620 |

BA: butyl acrylate
MTPDS: terminal-modified polydimethylsiloxane crosslinking agent
EGDMA: ethylene glycol dimethacrylate
AMA: allyl methacrylate
MMA: methyl methacrylate Experimental Example 2

In order to evaluate impact strength, tensile strength, surface gloss, and colorability of the molded article molded from the thermoplastic resin composition containing the core-shell copolymers prepared in Examples 1 to 7 and Comparative Examples 1 to 4 as an impact modifier, a specimen of the thermoplastic resin composition was prepared and evaluated by the following methods. The results are shown in Tables 3 to 6.

Izod impact strength: The ⅛ inch notched specimen was evaluated by the ASTM D256 test method. In this case, the measurements were all performed in chambers Tensile strength (50 mm/min, kg/cm$^2$): According to ASTM D638 method, a ⅛ inch dumbbell-shaped specimen was pinched by a jaw of an Instron tensile strength meter and pulled under a speed of 50 mm/min to measure the load at the time of cutting, and then the measured load (kg) at the time of cutting was calculated by dividing the product by thickness (cm) and width (cm) of the specimen.

Surface gloss: For the specimen of the prepared thermoplastic resin composition, the surface gloss at 45° angle was measured using a UD machine, which is a gloss meter manufactured by Toyo Seiki Co., Ltd., Japan. The higher the 45° gloss, the better the surface gloss.

Colorability: L* value of the specimen was measured using a color difference meter (Color Quest II, Hunter Lab Co.) according to ASTM D1925. The lower the L* value of the specimen, the better the colorability.

<Polycarbonate Resin Composition>

As shown in Tables 3 and 4, 0.1 parts by weight of lubricant and 0.05 parts by weight of antioxidant were added and mixed with a total of 100 parts by weight of the polycarbonate resin (PC1300-15, manufactured by LG Chemical) and the core-shell copolymer powder prepared in Examples and Comparative Examples. The resulting mixture was prepared in the form of pellets by a 40 pie extrusion kneader at a cylinder temperature of 300° C., and the pellets were injected to prepare a physical property specimen to measure the following physical properties. The results are shown in Tables 3 and 4. In the case, the contents of the polycarbonate resin and the core-shell copolymer powder are as shown in Tables 3 and 4.

TABLE 3

| Classification | | Examples | | | | | | |
|---|---|---|---|---|---|---|---|---|
| | | 1 | 2 | 3 | 4 | 5 | 6 | 7 |
| Polycarbonate composition | Polycarbonate resin (parts by weight) | 96 | 96 | 96 | 96 | 96 | 96 | 96 |
| | Core-shell copolymer (parts by weight) | 4 | 4 | 4 | 4 | 4 | 4 | 4 |
| Room temperature (23° C.) impact strength | 1/8" (kgf · cm/cm) | 76.7 | 77.5 | 77.1 | 75.1 | 76.1 | 75.9 | 75.5 |
| Low-temperature (−30° C.) impact strength | 1/8" (kgf · cm/cm) | 28.1 | 28.5 | 30.0 | 27.9 | 30.8 | 21.0 | 31.3 |
| Tensile strength | 50 mm/mim, Kg/cm² | 674 | 669 | 681 | 680 | 682 | 678 | 680 |
| Surface gloss | 45° | 104.5 | 104.6 | 104.5 | 103.5 | 103.5 | 103.4 | 104.0 |

TABLE 4

| Classification | | Comparative Examples | | | |
|---|---|---|---|---|---|
| | | 1 | 2 | 3 | 4 |
| Polycarbonate composition | Polycarbonate resin (parts by weight) | 96 | 96 | 96 | 96 |
| | Core-shell copolymer (parts by weight) | 4 | 4 | 4 | 4 |
| Room temperature (23° C.) impact strength | 1/8"(kgf · cm/cm) | 76.5 | 77.0 | 75.8 | 74.8 |
| Low-temperature (−30° C.) impact strength | 1/8"(kgf · cm/cm) | 20.5 | 21.3 | 21.0 | 30.7 |
| Tensile strength | 50 mm/mim, Kg/cm2 | 680 | 674 | 675 | 676 |
| Surface gloss | 45° | 104.6 | 104.0 | 103.4 | 92.1 |

Meanwhile, in order to confirm colorability of the polycarbonate resin composition, 0.1 parts by weight of lubricant and 0.1 parts by weight of antioxidant were added and mixed with a total of 102 parts by weight of the polycarbonate resin (PC1300-22, manufactured by LG Chemical), Black currant as a colorant, a phosphorus-based flame retardant (PX-200), and the core-shell copolymer powder prepared in Examples and Comparative Examples as shown in Tables 5 and 6 below. The resulting mixture was prepared in the form of pellets by a 40 pie extrusion kneader at a cylinder temperature of 260° C., and the pellets were injected to prepare a physical property specimen to measure the following physical properties. The results are shown in Tables 5 and 6. In the case, the contents of polycarbonate resin, Black currant, a phosphorus-based flame retardant, and the core-shell copolymer powders are as shown in Tables 5 and 6.

TABLE 5

| Classification | | Examples | | | | | | |
|---|---|---|---|---|---|---|---|---|
| | | 1 | 2 | 3 | 4 | 5 | 6 | 7 |
| Polycarbonate composition | Polycarbonate resin (parts by weight) | 79 | 79 | 79 | 79 | 79 | 79 | 79 |
| | Core-shell copolymer (parts by weight) | 10 | 10 | 10 | 10 | 10 | 10 | 10 |
| | Phosphorus-based flame retardant (parts by weight) | 11 | 11 | 11 | 11 | 11 | 11 | 11 |
| | Black currant (parts by weight) | 2 | 2 | 2 | 2 | 2 | 2 | 2 |
| Room temperature (23° C.) impact strength | 1/8" (kgf · cm/cm) | 52.0 | 50.2 | 58.9 | 59.0 | 58.5 | 58.7 | 58.1 |
| Low-temperature (−30° C.) impact strength | 1/8" (kgf · cm/cm) | 24.0 | 23.8 | 25.3 | 25.9 | 25.9 | 20.0 | 28.1 |
| Tensile strength | 50 mm/mim, Kg/cm² | 610 | 615 | 608 | 612 | 610 | 620 | 625 |
| Surface gloss | 45° | 96.5 | 96.6 | 95.6 | 95.7 | 95.5 | 95.7 | 95.4 |
| Colorability | L* | 28.4 | 28.4 | 28.4 | 28.5 | 28.5 | 28 | 30.0 |

TABLE 6

| Classification | | Comparative Examples | | | |
|---|---|---|---|---|---|
| | | 1 | 2 | 3 | 4 |
| Polycarbonate composition | Polycarbonate resin (parts by weight) | 79 | 79 | 79 | 79 |
| | Core-shell copolymer (parts by weight) | 10 | 10 | 10 | 10 |
| | Phosphorus-based flame retardant (parts by weight) | 11 | 11 | 11 | 11 |
| | Black currant (parts by weight) | 2 | 2 | 2 | 2 |
| Room temperature (23° C.) impact strength | ⅛"(kgf · cm/cm) | 50.8 | 58.3 | 53.4 | 60.4 |
| Low-temperature (−30° C.) impact strength | ⅛"(kgf · cm/cm) | 20.1 | 21.3 | 20.4 | 25.8 |
| Tensile strength | 50 mm/mim, Kg/cm² | 604 | 620 | 615 | 615 |
| Surface gloss | 45° | 96.4 | 96.2 | 95.5 | 86.1 |
| Colorability | L* | 28.4 | 28.4 | 28.4 | 28.4 |

As shown in Tables 3 to 6, it could be confirmed that according to the present invention, the molded article molded from the polycarbonate resin composition containing the core-shell copolymer including the terminal-modified polydimethylsiloxane crosslinking agent-derived crosslinking part in a core as an impact modifier, has excellent room temperature and low-temperature impact strengths, as well as excellent tensile strength, surface gloss, and colorability.

Meanwhile, in the case of Comparative Examples 1 and 2 using ethylene glycol dimethacrylate instead of a terminal-modified polydimethylsiloxane crosslinking agent-derived crosslinking part according to the present invention, it could be confirmed that low-temperature impact strength was reduced.

In addition, in the case of Comparative Example 3, it could be confirmed that the molded article molded from a polycarbonate resin composition containing a core-shell copolymer including a terminal-modified polydimethylsiloxane crosslinking agent-derived crosslinking part according to the present invention in the shell, not the core, as an impact modifier, had a reduced low-temperatures impact strength.

In addition, in the case of for Comparative Example 4 using a core-shell copolymer including a core having an average particle diameter greater than 500 nm as an impact modifier, it could be confirmed that the molded article molded from the polycarbonate resin composition had a reduced 45° gloss.

From the results as described above, the inventors confirmed that in the case of using a core-shell copolymer including a terminal-modified polydimethylsiloxane crosslinking agent-derived crosslinking part in a core as an impact modifier, the low-temperature impact strength may be particularly improved without deteriorating colorability.

The invention claimed is:

1. A core-shell copolymer, comprising:
a core; and
a shell surrounding the core,
wherein the core includes a first repeating unit derived from a first alkyl(meth)acrylate monomer having 1 to 8 carbon atoms and a crosslinking part derived from a terminal-modified polydimethylsiloxane crosslinking agent,
wherein the terminal-modified polydimethylsiloxane crosslinking agent includes a part modified by a second alkyl(meth)acrylate monomer at both terminals of polydimethylsiloxane, and
wherein the first repeating unit is present in an amount of 70 parts by weight to 95 parts by weight, and the crosslinking part is present in an amount of 0.01 parts by weight to 5 parts by weight, based on 100 parts by weight of the core-shell copolymer.

2. The core-shell copolymer of claim 1, wherein the core has an average particle diameter of 150 nm to 500 nm.

3. The core-shell copolymer of claim 1, wherein the core has an average particle diameter of 185 nm to 260 nm.

4. The core-shell copolymer of claim 1, wherein the terminal-modified polydimethylsiloxane crosslinking agent includes a terminal-modified polydimethylsiloxane crosslinking agent represented by Formula 1:

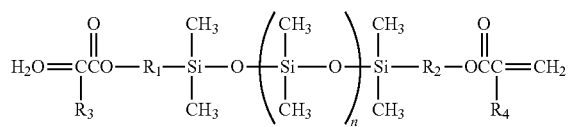

[Formula 1]

wherein $R_1$ and $R_2$ are each independently an alkylene group having 1 to 30 carbon atoms, $R_3$ and $R_4$ are each independently hydrogen or a methyl group, and n is 5 to 400.

5. The core-shell copolymer of claim 4, wherein $R_1$ and $R_2$ are each independently an alkylene group having 1 to 8 carbon atoms, and n is 10 to 330.

6. The core-shell copolymer of claim 1, wherein the first repeating unit is present in an amount of 80 parts by weight to 95 parts by weight, and the crosslinking part is present in an amount of 0.01 parts by weight to 5 parts by weight, based on 100 parts by weight of the core-shell copolymer.

7. The core-shell copolymer of claim 1, wherein the first repeating unit is present in an amount of 83 parts by weight to 88 parts by weight, and the crosslinking part is present in an amount of 0.1 parts by weight to 2 parts by weight, based on 100 parts by weight of the core-shell copolymer.

8. The core-shell copolymer of claim 1, wherein the core includes a seed.

9. The core-shell copolymer of claim 8, wherein the seed is included at 0.5 parts by weight to 20 parts by weight, based on 100 parts by weight of the core-shell copolymer.

10. The core-shell copolymer of claim 1, wherein the shell includes at least one repeating unit derived from third alkyl(meth)acrylate monomer or an aromatic vinyl monomer.

11. The core-shell copolymer of claim 1, wherein the core-shell copolymer includes 70 parts by weight to 95 parts by weight of the core and 5 parts by weight to 30 parts by weight of the shell, based on 100 parts by weight of the core-shell copolymer.

12. A method for preparing the core-shell copolymer of claim 1, the method comprising:
polymerizing a core-forming mixture including the first alkyl(meth)acrylate monomer having 1 to 8 carbon atoms and the terminal-modified polydimethylsiloxane crosslinking agent to prepare the core; and
polymerizing a shell-forming mixture in the presence of the prepared core to prepare the shell.

13. The method of claim 12, wherein the prepared core has an average particle diameter of 150 nm to 500 nm.

14. A thermoplastic resin composition comprising the core-shell copolymer of claim 1 and a polycarbonate resin.

15. The thermoplastic resin composition of claim 14, wherein the thermoplastic resin composition comprises 1 part by weight to 20 parts by weight of the core-shell copolymer, based on 100 parts by weight of the polycarbonate resin.

* * * * *